United States Patent [19]

Kirsch

[11] Patent Number: 4,993,946
[45] Date of Patent: Feb. 19, 1991

[54] THERMAL TOOTH PULP TESTER

[76] Inventor: Alan Kirsch, 1080 Squirrel Rd., Jenkintown, Pa. 19046

[21] Appl. No.: 454,444

[22] Filed: Dec. 21, 1989

[51] Int. Cl.$^5$ .............................................. A61C 3/00
[52] U.S. Cl. ...................................................... 433/32
[58] Field of Search .................. 433/32; 128/399, 400, 128/401; 406/27, 28

[56] References Cited

U.S. PATENT DOCUMENTS

| | | | |
|---|---|---|---|
| 2,949,107 | 8/1960 | Ziegler | 433/32 |
| 3,618,590 | 11/1971 | Yardley et al. | 433/32 |
| 3,919,775 | 11/1975 | Malmin | 433/32 |
| 4,164,214 | 8/1979 | Stark et al. | 433/32 |
| 4,197,641 | 4/1980 | Paulke et al. | 433/32 |
| 4,308,012 | 12/1981 | Tamler et al. | 433/32 |
| 4,350,488 | 9/1982 | Davis | 433/32 |
| 4,527,560 | 7/1985 | Masreliez | 433/32 |

Primary Examiner—Gene Mancene
Assistant Examiner—Michael Lynch
Attorney, Agent, or Firm—Gregory J. Gore

[57] ABSTRACT

A thermal tooth tester includes a handpiece which carries circulating water from a heated reservoir through an applicator tip located at the end of the handpiece. The reservoir includes a circulation pump and a temperature control with sensing means to accurately control the temperature of the circulating fluid and, hence, the temperature of the applicator tip. The handpiece further includes a replaceable disposable tip sheath to provide a clean antiseptic surface for each use.

5 Claims, 1 Drawing Sheet

THERMAL TOOTH PULP TESTER

FIELD OF THE INVENTION

This invention relates to dental equipment used for diagnosing the condition of human teeth. More specifically, it pertains to testing the health of the human tooth pulp.

PRIOR ART AND BACKGROUND OF THE INVENTION

The health and vitality of the tooth is often tested by tooth sensitivity to either thermal or electrical stimulus. Electric pulp testing, which requires passing an electric current through the teeth, is the more sophisticated procedure, however, there are various drawbacks. The electric pulp tester is not a full-proof instrument and there are conditions when a tooth with a necrotic pulp or partially necrotic pulp may cause a positive response to the electrical stimulus. Conversely, a tooth with a sound vital pulp may cause no response to the electrical stimulus. Thermal pulp testing is often a much more reliable and easily performed diagnostic procedure.

A thermal test is carried out by applying either heat or cold to the tooth. Cold tests are easily performed with ice or ethyl chloride spray. A hot test is performed by either applying a heated instrument or heated gutta-percha material at a temperature of over 150 degrees F. to the tooth. In the case of a tooth with a cast crown, which is too thick to allow the heated gutta-percha to raise the temperature of the underlying tooth's structure sufficiently to react, an alternative method of producing heat is utilized. A rubber wheel mounted on a mandrel, revolving at a polishing speed, is applied against the precious metal. The friction of the rubber wheel against the tooth produces a great amount of heat quickly.

Although the thermal tests are often considered the most accurate indicator of pulp health and vitality, and especially valuable in detecting pulpitis and in helping to differentiate reversible and irreversible pulp inflammation, there is heretofore no known testing procedure or related equipment which permits the controlled, repeatable and safe application of heat to a tooth at a known temperature level. The presently known methods of heating dental materials, instruments, or creating heat by friction with a rubber wheel are all highly uncontrolled and, hence, less reliable means of accurate diagnosis.

SUMMARY OF THE INVENTION

In order to meet the needs of a reliable and accurate heat applicator to test thermal tooth pulp sensitivity, the present thermal probe has been devised. The device includes a handpiece which carries circulating water from a heated reservoir through an applicator tip. The reservoir includes a circulation pump and a temperature control with sensing means to accurately control the temperature of the circulating fluid. The handpiece includes a replaceable, disposable tip to provide a clean, antiseptic surface for each use. The tip is narrow and pointed so that the heat may be very localized to individual teeth, or a point on a given tooth.

Further objects and advantages of the present invention will be readily apparent to those of skill in the art from the following drawings and description of the preferred embodiment.

DESCRIPTION OF THE PREFERRED EMBODIMENT

Figure 1:
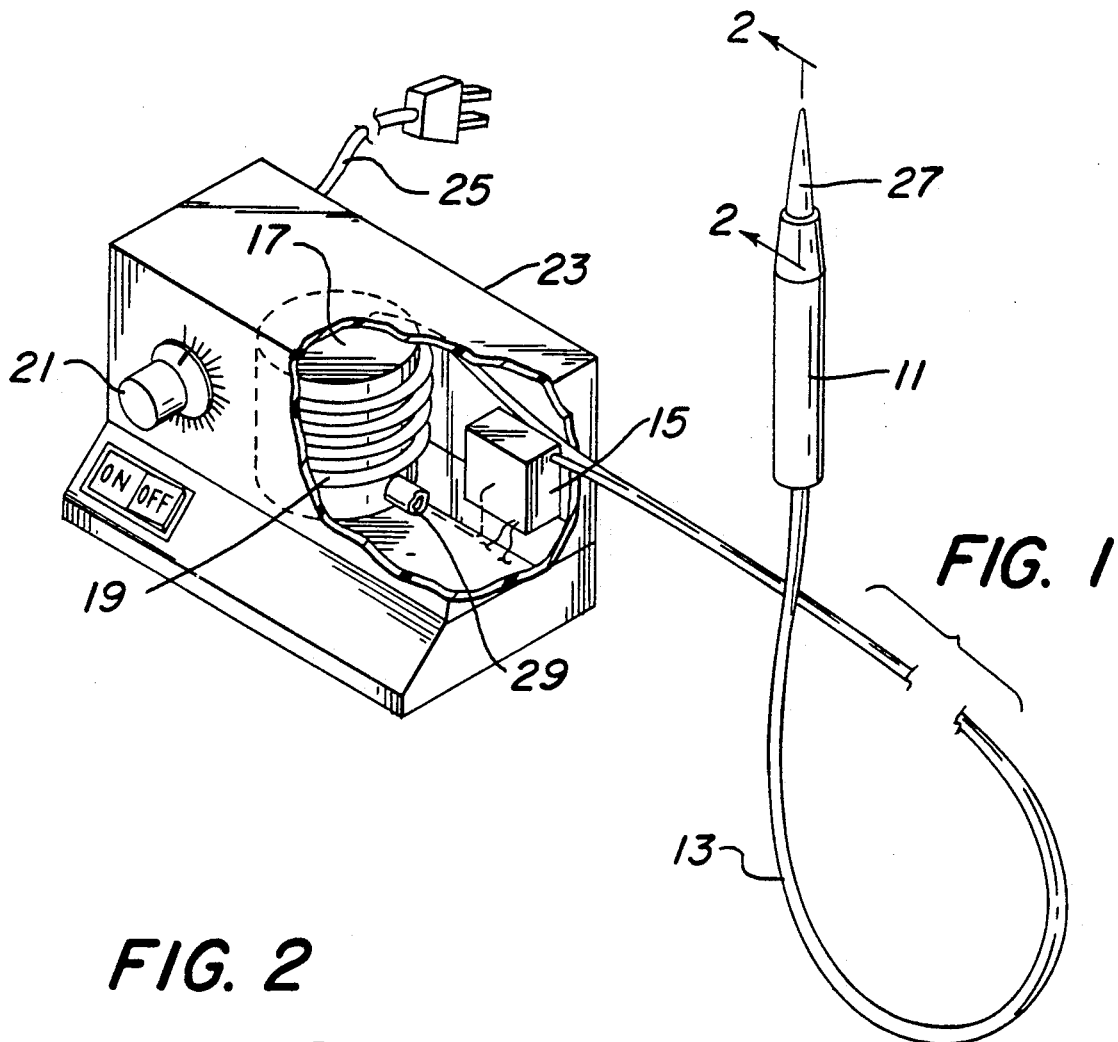
FIG. 1 is a top, front isometric view and partial cutaway view of the present device.

Referring now to FIG. 1, an elongate pencil-shaped handpiece 11, is connected to base cabinet 23 by means of a dual-circuit tubing 13. The base cabinet houses a fluid reservoir 17 which is heated by means of electric heating element 19. At the base of the reservoir, an outlet port 29 delivers fluid to pump 15 for circulation through tubing 13. Electric heating element 19 is controlled by a thermostat or temperature control 21 which maintains the circulating fluid at a pre-selected temperature. The thermostat 21 is connected to an appropriate temperature sensor and associated electrical circuitry well-known in the electrical arts and not further depicted here. Electrical supply to the components within the base cabinet is provided by line 25. Handpiece 11 includes disposable tip sheath 27 which is replaced after each use to maintain the instrument in an antiseptic condition, since it is used as an intraoral probe. The reservoir capacity and flow rate is selected to be sufficient to maintain the applicator tip at a constant temperature above 150 degrees F. Although any flowable liquid can be used for the circulating fluid, it is anticipated that water would be selected as the best choice because of its availability, thermal conductivity and low cost.

Figure 2:
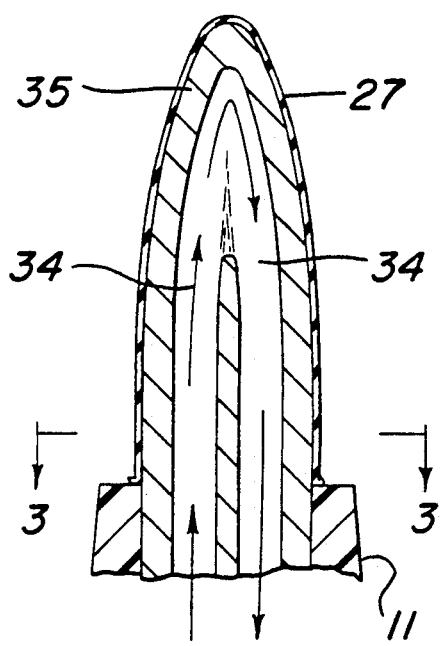
FIG. 2 is a side, sectional view of the handpiece taken from FIG. 1 as indicated in that figure.

Referring now to FIG. 2, a longitudinal cross-section of the cylindrical handpiece is shown which further depicts the details of the applicator tip 35. The arrows in this figure show the direction and circulation of the fluid 34 through the tip. Disposable sheath 27 fits tightly around the tip to ensure the highest degree of thermal conductivity. The sheath 27 extends from the endmost tip to the body of the handpiece 11.

Figure 3:
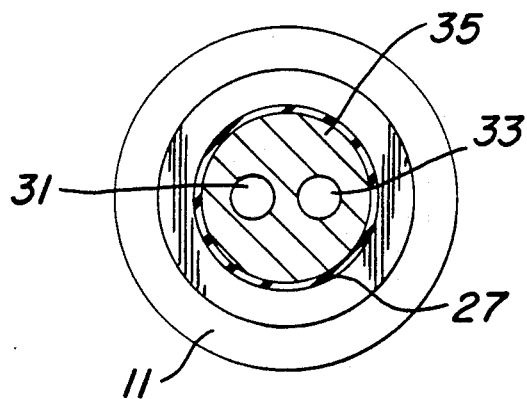
FIG. 3 is a cross-sectional view taken from FIG. 2 as shown in that figure.

Referring now to FIG. 3, a cross-section of the applicator tip 35 is shown. Inlet and return ports 31 and 33, respectively, are circular conduits formed in the body of tip 35 which may be made from a highly thermally conductive material, such as aluminum. Replaceable sheath 27 encircles and completely covers the applicator tip 35.

The present device is extremely easy to use. After the base components are activated, a short warm-up time is required until the selected temperature is reached. A new, disposable sheath is fitted about the end of the applicator tip and the dentist then may begin using the handpiece as a intraoral thermal probe applying the surface of the sheathed applicator tip against selected areas of the patient's teeth to be tested. The thermal testing is therefore safely administered as described above, since no electricity is introduced into the mouth of the patient and there are there no electrical lines in the hands of the dentist or close to the patient's body. When water is used as a circulating fluid, any possible leakage through the handpiece and the mouth of the patient would, of course, be non-toxic.

It should be understood that the above description discloses specific embodiments of the present invention and are for purposes of illustration only. There may be other modifications and changes obvious to those of ordinary skill in the art which fall within the scope of the present invention which should be limited only by the following claims and their legal equivalents.

What is claimed is:

1. An intraoral thermal probe for testing the vitality of the pulp of human teeth, comprising:
   a. an elongate, pencil-shaped handpiece, including a heat applicator tip at one end;
   b. a pair of conduits located within and extending substantially the entire length of said handpiece forming a inlet and return means for a circulating fluid passing through and reversing its direction within the applicator tip of said handpiece;
   c. a fluid reservoir containing a circulating fluid connected by tubing to said handpiece conduits for providing a source of fluid thereto;
   d. pump means hydraulically connected between an outlet port of said reservoir and said tubing for creating a circulating flow of said fluid from said reservoir to said handpiece and then returning to said reservoir; and
   e. a heating element in thermal communication with said fluid for increasing the temperature of said fluid and maintaining it at a pre-selected level.

2. The intraoral thermal probe of claim 1 further including a disposable sheath surrounding the applicator tip of the handpiece.

3. The intraoral thermal probe of claim 2 further including a base cabinet which houses said reservoir and said pump means and provides for the external mounting of a thermostatic control electrically connected to said heating element.

4. The intraoral thermal probe of claim 3 wherein said heating element encircles the outer wall of said fluid reservoir.

5. The intraoral thermal probe of claim 4 wherein said circulating fluid is water.

* * * * *